| United States Patent [19]
Fukawa et al.

[11] Patent Number: 4,652,581
[45] Date of Patent: Mar. 24, 1987

[54] TETRAHYDROINDOLE DERIVATIVE AS MEDICAMENT FOR CEREBRAL APOPLEXY

[75] Inventors: Kazunaga Fukawa, Yorozu; Kazuyoshi Bando, Kanagawa; Yoshikazu Hatanaka, Tokyo; Kikuo Nakazato, Kanagawa, all of Japan

[73] Assignee: Grelan Pharmaceutical Co., Ltd., Tokyo, Japan

[21] Appl. No.: 749,444

[22] Filed: Jun. 27, 1985

Related U.S. Application Data

[63] Continuation of Ser. No. 572,381, Jan. 28, 1984, abandoned.

[30] Foreign Application Priority Data

Jan. 24, 1983 [JP] Japan ................................ 58-8800
Dec. 16, 1983 [JP] Japan ............................ 58-236020

[51] Int. Cl.⁴ ............................................. A61K 31/40
[52] U.S. Cl. ................................................. 514/418
[58] Field of Search ....................................... 514/418

[56] References Cited

PUBLICATIONS

Beilock et al, Journal of the Chemical Society, 1951, pp. 712–716.
Drago et al, C.A. vol. 91(1929), 134075r.
Prato et al, C.A. vol. 93(1980), 161024w.
Hirumu et al, C.A. vol. 52(1958) 4866i.
Hirumu et al, Osaka Shiritsu Daigakau Igaku Zasshi, 6(1957), 793–9.

Primary Examiner—Allen J. Robinson

[57] ABSTRACT

1-Isopropyl-3-hydroxy-5-semicarbazono-6-oxo-2,3,5,6-tetrahydroindole, inclusive of pharmacologically acceptable salts thereof, is effective for prophylaxis and treatment of cerebral apoplexy.

9 Claims, No Drawings

TETRAHYDROINDOLE DERIVATIVE AS MEDICAMENT FOR CEREBRAL APOPLEXY

This application is a continuation of Ser. No. 572,381, filed Jan. 20, 1984 now abandoned.

This invention relates to a therapeutic means for prophylaxis or treatment of cerebral apoplexy.

More particularly, this invention relates to a medicament containing 1-isopropyl-3-hydroxy-5-semicarbazono-6-oxo-2,3,5,6-tetrahydroindole, inclusive of a pharmacologically acceptable salt thereof, for prophylaxis or treatment of cerebral apoplexy.

Cerebral apoplexy is caused by cerebral infarction (cerebral embolism or cerebral thrombosis) or cerebral hemorrhage.

The introduction of CT (computed tomography scanning) has made it possible for the first time to differentiate cerebral hemorrhage from cerebral infarction as the causes of cerebral apoplexy and thus has expedited studies of cerebral circulatory disorders. However, there are no adequate models developed for therapeutic studies, especially for cerebral infarction.

Clinical observations and CT studies have recently revealed that the following four stages are involved in the course of cerebral infarction: the first stage or ischemic stage at which convulsion and neurologic dysfunction are caused by vascular occlusion etc., the second stage or edematous stage at which the cerebral structure is affected and consciousness is disturbed, the third stage or hemorrhagic infarct stage at which blood-brain barrier disorder manifests itself, leading to an extended range of disorders due to extravascular extravasation of various substances, and the fourth stage or encephalatrophic stage at which cicatrization takes place as a result of vasogeneration or gliosis.

For the treatment at the first stage, the use of an anticoagulant or urokinase to dissolve thrombus has been proposed. However, any model capable of supporting the effect thereof is not available. The effect of such agent is being disputed from the clinical viewpoint. The second stage can be treated with glycerol or mannitol, which is reported to be clinically effective. At the fourth stage, a cerebral vasodilator or cerebral catalytic agent is used so as to activate the remaining normal brain moiety. However, there has not been found yet any therapeutic agent usable for hemorrhagic infarction by which the range of disorders is expanded after revascularization, and consequently, for cerebral apoplexy due to hemorrhagic infarction.

When cerebral hemorrhage occurs, the nerve cells destroyed by the direct contact with the blood cannot be repaired, and the therapeutic measure is nothing more than controlling the blood pressure in a hypertensive patient to prevent further cerebral hemorrhage by administering to such a patient a hypotensive drug such as a β-blocker, which is a temporizing one so as not to extend the lesion further.

Under the above-mentioned clinical and technical circumstances, the present inventors conducted an extensive research, using experimental cerebral infarction in rats as the animal model for human cerebral infarction and strokeprone spontaneously hypertensive rats as one for human cerebral hemorrhage, for the purpose of establishing an effective therapeutic measure for cerebral apoplexy, and unexpectedly found that 1-isopropyl-3-hydroxy-5-semicarbazono-6-oxo-2,3,5,6-tetrahydroindole is highly effective against hemorrhagic infarction as well as cerebral hemorrhage. The finding was followed by further studies which have resulted in the accomplishment of this invention.

Thus, the principal object of this invention is to provide a method for prophylaxis or treatment of cerebral apoplexy in a mammal suffering from a cerebral infarction or cerebral hemorrhage, which comprises administering to the mammal 1-isopropyl-3-hydroxy-5-semicarbazono-6-oxo-2,3,5,6-tetrahydroindole [also called 1-isopropylnoradrenochromemonosemicarbazone; hereinafter briefly referred to as ISI]. Another object of this invention is to provide a pharmaceutical composition comprising ISI, which is usable in the above-mentioned method. Other objects will be made clear from the disclosure and claims hereinafter.

The medicament according to the invention contains ISI as active ingredient. Thus, the medicament consists of ISI alone or of ISI and a pharmaceutically acceptable additive or additives.

ISI may be produced by a per se known method described e.g. in Journal of The Chemical Society, 1951, pages 712-716.

ISI to be used in the invention includes not only its free base form but also pharmacologically acceptable salt forms. Examples of such salts are salts with inorganic acids represented by mineral acids such as hydrochloric acid, hydrobromic acid, phosphoric acid and sulfuric acid, and salts with organic acids such as acetic acid, methanesulfonic acid, tartaric acid, lactic acid, fumaric acid, succinic acid and maleic acid.

The medicament according to the invention is administered orally or parenterally.

For oral administration, the above-mentioned additive or additives may be any of those ingredients which can serve as constituents of oral preparations and are generally selected from among known pharmaceutical ingredients such as carrier, vehicles or diluent (e.g. starch, lactose), binders (e.g. cellulose, polyvinyl pyrrolidone), disintegration adjusting agents (e.g. carboxymethyl cellulose), lubricants (e.g. magnesium stearate) and coating agents. The oral preparations may optionally contain further known pharmaceutical additives such as colors, flavors, preservatives, emulsifing agents and so on. Thus, the medicament according to the invention may take such oral preparation forms as tablets, granules, fine granules, powders, syrups and capsules.

These oral preparations usually contain ISI or a pharmacologically acceptable salt thereof in a proportion of about 0.1-10 weight % relative to the total weight of the preparations.

For injection, those ingredients which serve as constituents of aqueous injectable solutions are used as the above-mentioned additive or additives. Generally used are solvents (e.g. water) or solubilizers (e.g. propylene glycol), suspending agents (surfactant such as polysorbate), pH-adjusting agents (e.g. citric acid, lactic acid or salts thereof), stabilizers (e.g. sodium bisulfate) and other known injection constituents. The additive or additives may further be selected from among those known pharmaceutical ingredients which give a crystalline suspensoid injection to be dissolved at the time of administration by injection.

These injectable preparations usually contain ISI or a pharmacologically acceptable salt thereof at a ratio of about 0.001-0.5 weight % relative to the total weight of the preparations. In case of drops, the above injectable solutions can be used singly or in admixture with a humorsubstitute (e.g. substitution infusion or fluid therapy, blood substitutes, Ringer's solution or physiological saline) or any other pharmaceutical (e.g. a hemostat, chemotherapeutic agent or anticoagulant) compatible with the active ingredient of the present invention. These drops usually contains ISI or a pharmacologically acceptable salt thereof at a ratio of about 0.000001–0.1 weight %, more preferably about 0.00001–0.05 weight %, relative to the total weight of the drops.

For the manufacture of the desired oral or parenteral preparation using the above pharmaceutical ingredients, the manufacturing methods described in Japanese Pharmacopeia tenth edition (JP X) or methods similar thereto can be employed.

The subjects of administration of the drug according to this invention are mammals including human beings and these preparations can be used for the treatment or prophylaxis of cerebral apoplexy in humans. Especially, the present medicament can be used for cerebral apoplexy cases, the causes of which are not confirmed as being cerebral hemorrhage or cerebral infarction.

The dosage of the drug of this invention is usually about 1 to 50 mg, preferably about 2 to 20 mg in terms of free ISI per adult human patient per day for oral administration, and about 0.05 to 5 mg, preferably about 0.1 to 0.5 mg in terms of free ISI per adult human patient per day for injection. In case of drops, ISI may be used in a dose up to about 3 to 5 times of the above-mentioned injection dosage. The optimum dose can be determined according to the stage and condition of the disease, the patient's age, sex and body weight, and other factors.

The specific manner of administering the drug is described below.

When the drug according to this invention is used as a therapeutic agent, it is administered in the form of an injectable solution or an oral preparation to such patients suffering from cerebral infarction especially in the third stage referred to hereinbefore or from cerebral hemorrhage. In this case, if the patient has an elevated brain pressure and is in a risk state, a hypertonic solution having a brain pressure lowering action is preferably administered prior to the administration of the drug according to this invention. The hypertonic solution may be a solution containing glycerol, mannitol, glucose or the like. Depending on case, the hypertonic solution can be administered simultaneously with the drug according to this invention (for example, as a mixture of both) or administered even immediately after administration of the present drug. The dosage of the hypertonic solution may be selected within its usual range.

The medicament according to this invention can be used not only as a therapeutic agent but also as a prophylactic agent. For the latter purpose, it is administered in the form of an injection or an oral preparation to such patients as those in pre-third stages and patients with signs or risks of hemorrhagic infarction, and as those in danger of cerebral hemorrhage.

The procedures and results of clinical studies using ISI which is the active agent according to this invention are disclosed below.

TEST EXAMPLE 1

(A) A cerebral infarction model was constructed by the following procedure. The bilateral common carotid arteries of Sprague Dowley male rats (body weights 300 to 350 g) in which one of the vertebral arteries was occluded by electrocauterization in accordance with the method of W. Pulsinelli et al (Stroke 10, 267, 1979) were uniformly occluded and made repatent, using clamps, at an interval of 1 hour for the first cycle and thereafter at 30-minute intervals for a total of 4 cycles. This treatment caused some animals to convulse and die but produced in almost all the surviving animals hemispheric infarction mainly in the cortical branch.

After the final establishment of repatency in this test model and on the second day and onwards, 1 ml/100 g body weight of Glyceol ® Injection [a preparation containing 10 weight % of glycerol, the trademark of Chugai Pharmaceutical Co., Ltd., Japan] was intraperitoneally administered twice daily. The test drug ISI was dissolved in Glyceol ® Injection to a concentration of 0.08 weight % and administered in the same manner as Glyceol ® Injection.

In a disease model such as the one used in this experiment, death of animals occurs in many cases as an infarction leads to cerebral edema which compresses the brain stem. Therefore, for the purpose of preventing death due to this cause and ensuring a smooth performance of the experiment, the animals were treated with Glyceol ® Injection which has a relieving effect on cerebral edema.

The brains submitted to the study were obtained by bleeding the animals to death when they showed a dying condition or after 7 days and enucleating the brain from the skull. The isolated brains were fixed in 10% formalin. For the assessment of hemorrhagic infarction, paraffin-embedded specimens prepared from three different sections passing through the mid-point between the anterior portion of the frontal lobe and the optic chiasm, the optic chiasm and the posterior portion of the mamillary body were used after H.E. stain.

As compared with the control group, an inhibitory effect on hemorrhagic infarction was obtained in the ISI group at the significance level of 5% (See Table 1).

TABLE 1

| | Inhibitory effect of ISI injection on the onset of hemorrhagic infarction | | | |
|---|---|---|---|---|
| | Number of animals used | Number of deaths within 5 hours | Number of animals medicated | Number of cases of hemorrhagic infarction |
| Glyceol ® injection group | 20 | 0/20 | 20 | 6/20 |
| 0.08% ISI in Glyceol ® injection group | 20 | 1/20 | 19 | 1/19 |

(B) In the system using the above-mentioned cerebral infarction model, 0.25 ml/100 g body weight of suspension of the test drug ISI in 5% sodium alginate was orally administrated (dose of ISI: 30 mg/kg). To control animals, 0.25 ml/100 g body weight of 5% sodium alginate was orally administered. The administration schedule was twice daily for both groups.

The brains submitted to the study were subjected to the same treatment as above, and assessments were made on paraffin-embedded specimens.

As compared with the control group, an inhibitory effect on cerebral infarction was obtained in the ISI group at the significance level of 5% (Table 2).

TABLE 2

Inhibitory effect of ISI orally administered on the onset of hemorrhagic infarction

| | Number of animals used | Number of deaths within 5 hours | Number of animals medicated | Number of cases of hemorrhagic infarction |
|---|---|---|---|---|
| Sodium alginate group | 45 | 2/45 | 43 | 18/43 |
| Sodium alginate plus ISI group | 45 | 4/45 | 41 | 9/41 |

TEST EXAMPLE 2

Stroke-prone spontaneously hypertensive rats [K. Okamoto et al., Circulation Res. suppl. 34 & 35, 143 (1974)]of 10 weeks aged were fed, in conventional manner, with a 1 weight % aqueous solution of sodium chloride as drinking water [H. Ikeda et al., Europ. J. Pharmacol. 53, 173 (1979)]being employed.

Animals were subjected to periodical observation, three times a day, until the symptom of cerebral apoplexy was manifested in all the animals of the control group. The difference between the control group and the test group in the ranking of the symtoms of cerebral apoplexy manifested was subjected to rank sum test.

In the test group, each of the animals was orally treated every day with ISI dissolved in 1% gum-arabica solution so that the concentration may become 0.06 weight % at a dose of 0.5 ml/100 g body weight twice a day, starting with the sodium chloride loading. In the control group, each of the animals was treated with 1% gum-arabica solution at a dose of 0.5 ml/100 g body weight in a manner similar to that in the test group.

The animals in which the symptom of apoplexy was manifested, after being anesthetized, was treated with intravenous injection of 1% Evans Blue (dosage: 1 ml/kg). After sacrifice by bloodletting, hemorrhage and extravascular extravasation of the dye in the brain and the spinal cord was observed.

Each animal of both the groups was subjected to blood pressure measurement.

Although the change in blood pressure of the animals of both groups showed quite similar patterns as shown in Table 3, the effect of ISI against cerebral apoplexy was observed in the test group with 5% significant difference (Mann-Whitrey's U-test) as is clear from Table 4.

TABLE 3

Change of blood pressure before and after NaCl loading

| | Control Group | Test Group |
|---|---|---|
| Blood pressure on previous day of the loading | 201.7 ± 5.5 | 201.1 ± 5.5 |
| Blood pressure on seven days after the loading | 225.9 ± 3.5 | 229.1 ± 3.9 |

TABLE 4

Effect of ISI against cerebral apoplexy (C.A.)

| | Days after NaCl loading | 20 | 21 | 23 | 26 | 32 | 33 | 34 | 37 | 39 | 40 | 41 | 42 | Total |
|---|---|---|---|---|---|---|---|---|---|---|---|---|---|---|
| Number of animals suffering from C.A.* | Control group | 0 | 1 | 1 | 1 | 1 | 1 | 1 | 0 | 1 | 1 | 0 | 2 | 10/10 |
| | Test Group (ISI 3.0 mg/kg) | 1 | 0 | 0 | 0 | 0 | 1 | 0 | 2 | 0 | 0 | 1 | 0 | 5/10 |

With paralysis of the limbs, stereotyped behaviour, an extreme loss of body weight or any of the following symptoms was observed in the onimats, those animals were counted as those suffering from C.A.: Excitement, Hyperirritability, Depression, Epileptic symptom, Hemiplegia, Sudden death.

From the above test examples, it would be understood that the medicament of this invention are remarkably effective for prophylaxis and therapy of cerebral apoplexy due to cerebral infarction and cerebral hemorrhage, acting on both models of cerebral infarction aggravated by lowering of cerebral blood flow and of cerebral hemorrhage due to high blood pressure.

Acute toxicity of ISI ($LD_{50}$ in mice),
Oral: ≧10 g/kg,
Intravenous: 350 mg/kg.

PREPARATION EXAMPLE

1. Tablets
Formula for one tablet (180 mg)
ISI: 2 mg,
Crystalline cellulose: 60 mg,
Lactose: 50 mg,
Corn starch: Balance,
Hydroxypropylcellulose: 2 mg,
Magnesium stearate: 1 mg.

The above ingredients were weighed and mixed in the indicated proportions. Then, the tablet was prepared in accordance with the tablet manufacturing method set forth in Japanese Pharmacopeia X.

2. Injectable solution
Formula for one ampule of injection (5 ml),
ISI: 0.25 mg,
Sodium citrate: 5 mg,
Citric acid: 2 mg,
Propylene glycol: 160 mg,
Dried sodium sulfite: 2 mg,
Sodium chloride: 0.5 mg,
Distilled water for injection Balance.

The above ingredients were weighed and mixed in the indicated proportions and dissolved in the vehicle. The desired ampule preparation was manufactured in accordance with the injection manufacturing method set forth in Japanese Pharmacopeia X.

3. Injectable solution
Formula for one ampule of injection (10 ml),
Hydrochloride of ISI*: 1 mg,
Sodium chloride: 90 mg,
Distilled water for injection Balance.

*Hydrochloride of ISI is a new compound which can be prepared by, for example, adding 1.6 g of a 35.7 weight % methanolic solution of hydrochloric acid to a solution of 4 g of ISI in 250 ml of methanol, and recrystallizing from a mixture of methanol and ethyl ether to give 4.31 g of yellow crystals melting at 135° C. (decomposition).

The above ingredients were weighed and mixed in the indicated proportions and dissolved in the vehicle.

The desired ampule preparation was manufactured in accordance with the injection manufacturing method set forth in Japanese Pharmacopeia X.

4. A crystalline suspensoid injection

A vial was filled with 10 mg of hydrochloride of ISI and sealed. This preparation can be used as drops after dissolved in, for example, 100 ml of substitution infusion.

What is claimed is:

1. A method for the treatment of a mammal suffering from cerebral infarction or cerebral hemorrhage which serves to treat or avert cerebral apoplexy, and which comprises administering to the mammal, as an active ingredient, an effective amount of 1-isopropyl-3-hydroxy-5-semicarbazono-6-oxo-2-3-5-6- tetrahydroindole, inclusive of a pharmacologically acceptable salt thereof.

2. A method according to claim 1, wherein the cerebral apoplexy is due to cerebral hemorrhagic infarction.

3. A method according to claim 1, wherein the cerbral apoplexy is due to cerebral hemorrhage.

4. A method according to claim 1, wherein the mammal is human.

5. A method according to claim 1, wherein free 1-isopropyl-3-hydroxy-5-semicarbazono-6-oxo-2,3,5,6-tetrahydroindole is administered as the active ingredient.

6. A method according to claim 1, wherein the active ingredient is administered for the treatment of the cerebral apoplexy.

7. A method according to claim 1, wherein the active ingredient is administered orally or parenterally.

8. A method according to claim 7, wherein the active ingredient is orally administered to a human patient in a dosage of about 1 to 50 mg in terms of free 1-isopropyl-3-hydroxy-5-semicarbazono-6-oxo-2,3,5,6-tetrahydroindole per adult patient per day.

9. A method according to claim 7, wherein the active ingredient is administered intraveneously or intramuscularly to a human patient in a dosage of about 0.05 to 5 mg in terms of free 1-isopropyl-3-hydroxy-5-semicarbazono-6-oxo-2,3,5,6-tetrahydroindole per adult patient per day.

* * * * *

UNITED STATES PATENT AND TRADEMARK OFFICE
CERTIFICATE OF CORRECTION

PATENT NO. : 4,652,581
DATED : March 24, 1987
INVENTOR(S) : Fukawa et al.

It is certified that error appears in the above-identified patent and that said Letters Patent is hereby corrected as shown below:

In the title page, block [73], change the Assignee from "Grelan Pharmaceutical Co., Ltd., Tokyo, Japan" to --Takeda Chemical Industries, Ltd., Osaka, Japan--.

Signed and Sealed this

Second Day of August, 1994

Attest:

BRUCE LEHMAN

Attesting Officer

Commissioner of Patents and Trademarks